United States Patent
Reckefuss et al.

(10) Patent No.: US 9,358,815 B2
(45) Date of Patent: Jun. 7, 2016

(54) ARRANGEMENT FOR CAPTURING AN IMAGE OF A PRINTING SUBSTRATE WEB

(71) Applicant: eltromat GmbH, Leopoldshöhe (DE)

(72) Inventors: Klaus Reckefuss, Leopoldhöhe (DE); Frank Böttcher, Verl (DE)

(73) Assignee: eltromat GmbH, Leopoldshöhe (DE)

( * ) Notice: Subject to any disclaimer, the term of this patent is extended or adjusted under 35 U.S.C. 154(b) by 0 days.

(21) Appl. No.: 14/785,402

(22) PCT Filed: Mar. 27, 2014

(86) PCT No.: PCT/EP2014/056235
§ 371 (c)(1),
(2) Date: Oct. 19, 2015

(87) PCT Pub. No.: WO2014/177326
PCT Pub. Date: Nov. 6, 2014

(65) Prior Publication Data
US 2016/0075153 A1   Mar. 17, 2016

(30) Foreign Application Priority Data
Apr. 29, 2013 (DE) .................... 20 2013 101 851 U

(51) Int. Cl.
| | | |
|---|---|---|
| B41J 29/393 | (2006.01) | |
| B41J 13/00 | (2006.01) | |
| B41F 33/00 | (2006.01) | |
| G01N 21/89 | (2006.01) | |
| H04N 1/195 | (2006.01) | |
| G01N 21/898 | (2006.01) | |
| H04N 1/028 | (2006.01) | |

(52) U.S. Cl.
CPC ......... *B41J 13/0009* (2013.01); *B41F 33/0081* (2013.01); *G01N 21/8901* (2013.01); *B41P 2233/13* (2013.01); *G01N 21/8983* (2013.01); *H04N 1/0284* (2013.01); *H04N 1/19594* (2013.01); *H04N 2201/0081* (2013.01)

(58) Field of Classification Search
CPC .. B65H 2553/40; B65H 2553/41; B65H 7/14; B65H 23/0216; G01N 21/86; G01N 21/89; G01N 21/8901; G01N 21/8903; G01N 21/8915; G01N 2021/9511; G01N 2021/9583; G01N 21/9506; G03F 9/70; G01M 11/0278
See application file for complete search history.

(56) References Cited

U.S. PATENT DOCUMENTS

2003/0214656 A1*  11/2003  Yamaguchi ............ B41J 11/009
                                                                          356/445

FOREIGN PATENT DOCUMENTS

DE    102004022955 A1   12/2004
DE    102006016209 A1   10/2007

(Continued)

*Primary Examiner* — Julian Huffman
(74) *Attorney, Agent, or Firm* — Richard M. Goldberg

(57) ABSTRACT

An arrangement for capturing an image of a printing substrate web in a printing machine, includes a camera that has a sensor field extending parallel to the printing substrate web, and an objective lens an optical axis of which runs at right angles to the sensor field, a light source that is arranged relative to the printing substrate web such that the light emitted therefrom is reflected by reflective surface portions of the printing substrate web mainly into the camera, and the objective lens is arranged to be offset from the sensor field such that a straight line extending through the center of the sensor field and the center of the objective lens and a straight line extending from the center of the light source to the center of the light incident on the image field on the printing substrate web form equal angles with the axis of incidence.

5 Claims, 2 Drawing Sheets

(56) References Cited

FOREIGN PATENT DOCUMENTS

| | | | |
|---|---|---|---|
| DE | 102010007421 | B3 | 7/2011 |
| EP | 0338442 | A2 | 10/1989 |
| EP | 0541990 | A1 | 5/1993 |
| EP | 1619026 | A2 | 1/2006 |
| EP | 1623943 | A1 | 2/2006 |
| EP | 1940141 | A1 | 7/2008 |
| EP | 2468508 | A2 | 6/2012 |

* cited by examiner

ARRANGEMENT FOR CAPTURING AN IMAGE OF A PRINTING SUBSTRATE WEB

BACKGROUND OF THE INVENTION

The invention relates to an arrangement for capturing an image of a printing substrate web in a printing machine, comprising a camera that has a sensor field extending parallel to the printing substrate web, and an objective lens an optical axis of which runs at right angles to said sensor field, and comprising a light source that is arranged relative to the printing substrate web such that the light emitted therefrom is reflected by reflective surface portions of the printing substrate web mainly into the camera.

An image capturing arrangement of this type serves for example for generating a feedback signal for a register controller in a printing press. The light source shall be arranged so as to achieve a good image contrast, in particular also in those cases where the printing substrate web has a reflective surface or a least reflective surface parts, for example, when the printing substrate web is a reflective foil or is metallised or coated with a reflective lacquer.

For obtaining a high contrast between background (printing substrate) and the printed image, there exist on the one hand bright field illuminations wherein all reflective parts appear darker in the image, and on the other hand so-called coaxial illuminations wherein the beam paths from the light source to the printing substrate web and from the printing substrate web to the camera extend coaxially so that the light from the light source is reflected directly into the camera and consequently the reflective parts appear bright. Such a coaxial illumination has heretofore been achieved by means of semi-transparent mirrors, because otherwise the camera would obscure the light source or, conversely, the light source would obscure the camera. However, arrangements employing semi-transparent mirrors suffer from high losses in light intensity.

Another possibility is to arrange the light sources on a circle around the optical axis of the objective lens of the camera. In that case, however, a homogeneous illumination of the image field cannot be obtained.

SUMMARY OF THE INVENTION

It is an object of the invention to provide a coaxial illumination arrangement with homogeneous illumination of the image field and low losses in light intensity.

In order to achieve this object, the objective lens is arranged to be offset from the sensor field such that a straight line extending through the centre of the sensor field and the centre of the objective lens and a straight line extending from the centre of the light source to the centre of the light incident on the image field on the printing substrate web form equal angles with the axis of incidence.

With this arrangement, the light emitted from the light source is reflected at the reflective surface parts of the printing substrate web directly into the camera in accordance with the principle "incident angle equals emergent angle". On the other hand, the sensor field and the objective lens of the camera are oriented parallel to the plane of the printing substrate web, so that there will be only minimal image distortions, if any. Due to the offset between the objective lens and the sensor field, slightly different optical path lengths are obtained for image areas remote from the centre of incident light. However, by suitable choice of the focal length of the objective lens and suitable adjustment of the distance between the sensor field and the objective length it can be ensured that the image is focused sufficiently on the entire image area.

Useful details of the invention are indicated in the dependent claims.

BRIEF DESCRIPTION OF THE DRAWINGS

An embodiment example will now be described in conjunction with the drawings wherein.

DETAILED DESCRIPTION

Figure 1:
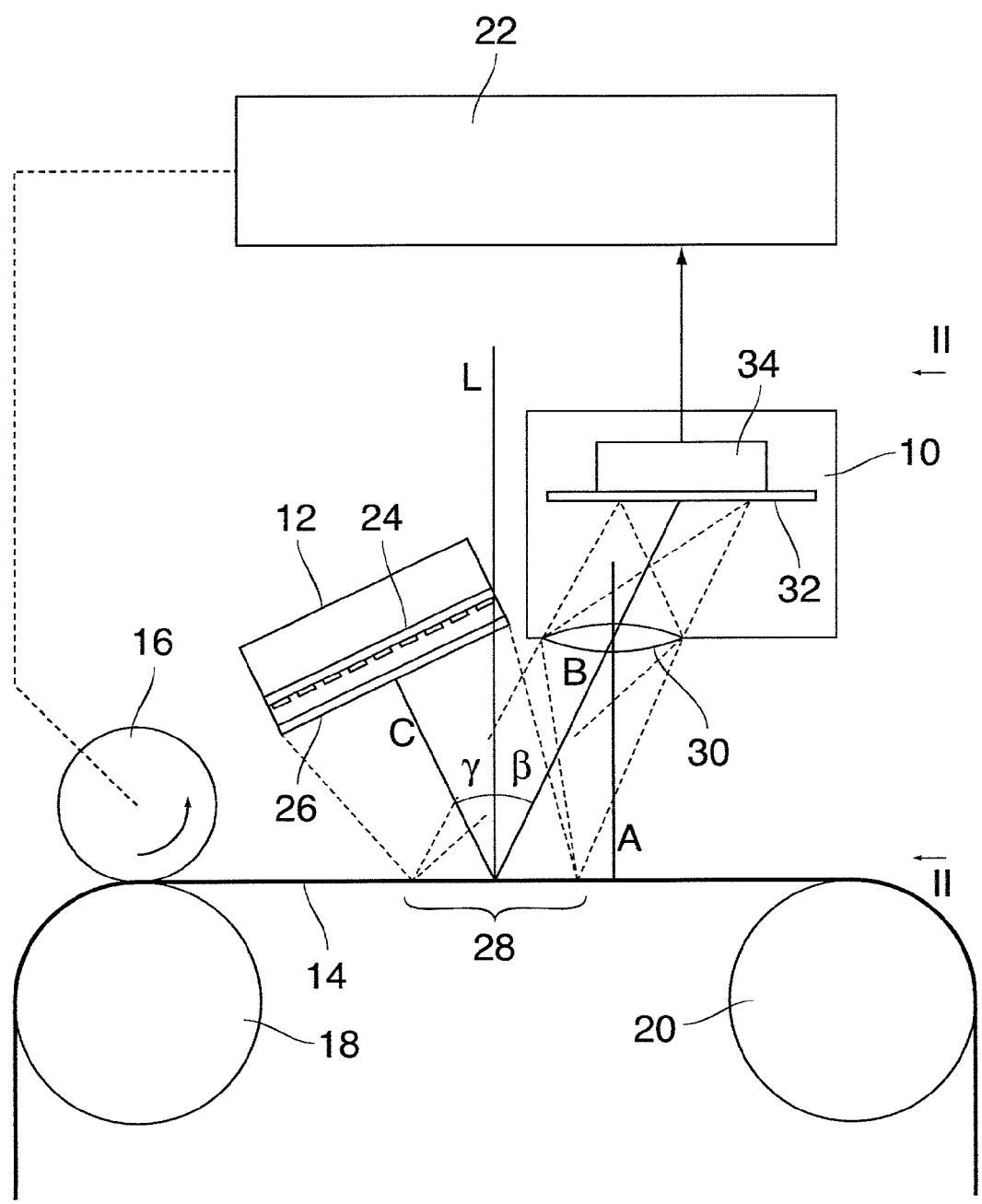
FIG. 1 a sketch showing the principle of an image capturing arrangement according to the invention in a printing press.

The image capturing arrangement shown in FIG. 1 comprises a camera 10 and a light source 12 which are arranged in a printing press in such a manner that an image that has been printed onto a printing substrate web 14 can be captured and processed electronically. Of the printing press, only a printing cylinder 16, a back pressure cylinder 18 and a guide cylinder 20 via which the printing substrate web 14 is withdrawn from the back pressure cylinder have been shown here. A register controller 22 processes the image captured by the camera 10 and controls the drive and the lateral position of the printing cylinder 16 such that the color component image that is printed with the printing cylinder 16 is in register with other color component images that are printed onto the printing substrate web with other printing decks which have not been shown here.

The light source 12 comprises a board 24 on which LEDs have been mounted and in front of which a diffusion disk 26 is arranged for diffusing the light from the LEDs. The light source is directed obliquely onto the surface of the printing substrate web 14, so that an image field 28 on the printing substrate web is illuminated homogeneously. A straight line C which passes from the centre of the light source 12 to the centre of the incident light on the printing substrate web, i.e. the centre of the image field 28, forms a non-zero angle $\gamma$ with the axis of incidence L.

The camera 10 has an objective lens 30 the optical axis A of which extends at right angles to the surface of the printing substrate web 14. A sensor field 32, such as a CCD-field, is arranged in the image plane of the objective lens 30. The image captured with the sensor field 32 is processed in camera electronics 34 and is transmitted to the register controller 22.

According to the invention, the optical axis A of the objective lens does not pass through the centre of the sensor field 32, but instead the objective lens is laterally offset such that a straight line B which passes from the centre of the sensor field 32 through the centre of the objective lens 30 to the centre of incident light on the image field 28 forms an angle $\beta$ with the axis of incidence L, which angle $\beta$ is equal to the angle $\gamma$. Therefore, the light of the light source 12 that is reflected at reflective surface parts of the printing substrate web 14 is transmitted directly into the camera along the straight line B, so that the reflective surface parts will appear bright in the image, in accordance with the principles of a coaxial illumination arrangement. Since, on the other hand, the sensor field 32 is parallel to the surface of the printing substrate web and the optical axis of the lens is orthogonal to the printing substrate web, distortions of the image are largely avoided in spite of the "slanting view of sight". Eventually, this permits to achieve a low-distortion image capture with coaxial illumination without the use of semi-transparent mirrors and consequently with high light intensity yield.

In the example shown, the board 24 and the diffusion disk 26 which is arranged parallel to the board 24 are inclined such that they form a right angle with the straight line C. It would however be possible to conceive also an arrangement wherein the board 24 and the diffusion disk are arranged to be parallel to the printing substrate web 14.

Figure 2:
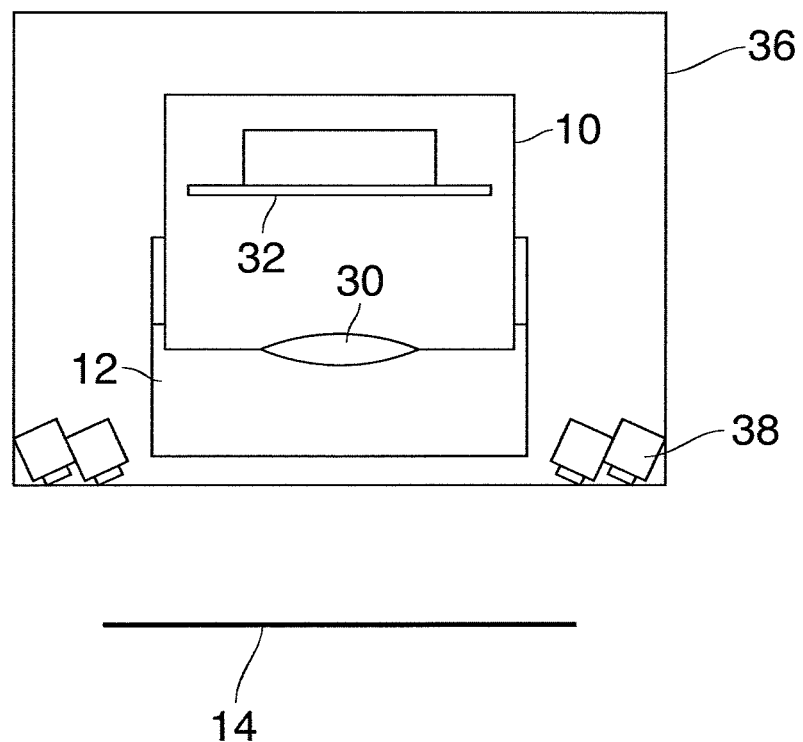
FIG. 2 is a view of the arrangement shown in FIG. 1 as seen from the direction of arrows II-II in FIG. 1.

FIG. 2 shows the image capturing arrangement in a view from the direction of the arrows II-II in FIG. 1. Also shown is a casing 36 in which the camera 10 and the light source 12 are mounted in appropriate positions and which is open towards the printing substrate web 14. Further, it can be seen in FIG. 2 that the objective lens 30 is centered onto the sensor field 32 in the direction normal to the plane of the drawing in FIG. 1 (in lateral direction in FIG. 2).

In the example shown, the casing 36 accommodates, in addition to the light source 12, a bright field illumination 38 formed by linear LED arrays that are arranged symmetrically on both sides of the objective lens 30. The reflective surface parts of the printing substrate web 14 do not reflect the light from these LED arrays into the camera 10, so that the camera will receive from these LED arrays essentially only the light that has been scattered diffusely at non-reflective surface parts of the printing substrate web.

The invention claimed is:

1. An arrangement for capturing an image of a printing substrate web in a printing machine, comprising:
   a camera including:
      a sensor field extending parallel to the printing substrate web, and
      an objective lens having an optical axis (A) which runs at right angles to said sensor field,
   a light source that is arranged relative to the printing substrate web such that light emitted therefrom is reflected by reflective surface portions of the printing substrate web mainly into the camera, and
   wherein the objective lens is arranged to be offset from the sensor field such that a straight line extending through a center of the sensor field and a center of the objective lens and a straight line extending from a center of the light source to a center of light incident on the image field on the printing substrate web form equal angles with the axis of incidence.

2. The arrangement according to claim 1, wherein the light source has a number of light emitting elements distributed over a surface of a board.

3. The arrangement according to claim 2, wherein:
   the light source has a diffusion disk for diffusing light that is to impinge onto the printing substrate web, and
   at least one of:
      the board and
      the diffusion disk
   are arranged to be inclined relative to the printing substrate web.

4. The arrangement according to claim 1 wherein the light source has a diffusion disk for diffusing light that is to impinge onto the printing substrate web.

5. The arrangement according to claim 1, further comprising at least one additional light source for a bright field illumination.

* * * * *